(12) United States Patent
Pauly

(10) Patent No.: US 6,224,889 B1
(45) Date of Patent: May 1, 2001

(54) ACTIVE COMPOSITION FOR COMBATING THE EFFECTS OF THE COLD AND COSMETIC PRODUCT CONTAINING THIS COMPOSITION

(75) Inventor: Gilles Pauly, Nancy (FR)

(73) Assignee: Laboratoires Serobiologiques (Societe Anonyme), Pulnoy (FR)

( * ) Notice: Subject to any disclaimer, the term of this patent is extended or adjusted under 35 U.S.C. 154(b) by 0 days.

(21) Appl. No.: 09/367,224

(22) PCT Filed: Jan. 30, 1998

(86) PCT No.: PCT/FR98/00180

§ 371 Date: Sep. 8, 1999

§ 102(e) Date: Aug. 8, 1999

(87) PCT Pub. No.: WO98/34590

PCT Pub. Date: Aug. 13, 1998

(30) Foreign Application Priority Data

Feb. 11, 1997 (FR) .................................................. 97 01711

(51) Int. Cl.⁷ .............................. A61K 7/00; A61K 7/42; A01N 37/18; A01N 43/04; A01N 37/12

(52) U.S. Cl. ................................ 424/401; 424/59; 514/2; 514/54; 514/60; 514/561

(58) Field of Search .......................... 424/401, 59; 514/2, 514/54, 60, 561

(56) References Cited

U.S. PATENT DOCUMENTS

| 4,565,643 | * | 1/1986 | Arai et al. ............................... 252/70 |
| 4,711,780 | | 12/1987 | Fahim . |
| 5,391,373 | | 2/1995 | Mausner . |
| 5,420,106 | | 5/1995 | Parab . |
| 5,571,503 | | 11/1996 | Mausner . |
| 5,660,838 | * | 8/1997 | Koga et al. .......................... 424/401 |

FOREIGN PATENT DOCUMENTS

| 1057277 | 2/1967 | (GB) . |
| WO 96/28008 | 9/1996 | (WO) . |

\* cited by examiner

Primary Examiner—Shelley A. Dodson
Assistant Examiner—Manna Lamm
(74) Attorney, Agent, or Firm—Young & Thompson

(57) ABSTRACT

Topical active composition against the effects of cold, which is constituted by 0.1% to 30% by weight of polysaccharides comprising at least glycogen and at least one mucilage extracted from conifer, by 45% to 95% by weight of vegetable proteins extracted from legumes and by 0.1% to 25% by weight of amino acids selected from the group consisting of threonine, serine, proline and alanine.

8 Claims, No Drawings

ACTIVE COMPOSITION FOR COMBATING THE EFFECTS OF THE COLD AND COSMETIC PRODUCT CONTAINING THIS COMPOSITION

The present invention relates to the field of protection against cold and the prevention of risks and the repair of damage connected with the action of cold, particularly as to the skin, and has for its object a composition active against the effects of cold, as well as a cosmetic product comprising such a composition.

It is well known that the cold to which the skin, in particular of the face, is subjected for several months of the year, gives rise to degradation of the epidermal cells, which translates in the aesthetic sense into the appearance of skin that is dry, sensitive, fragile and irritable. Moreover, these phenomena can only accelerate the process of cutaneous aging.

Thus, freezing kills most of the living cells and the ice crystals which form inside and outside the cells by freezing of the intra- and extra-cellular medium, tear the cellular membranes, and damage the subcellular organisms. The cells then empty their contents, and the cellular metabolisms are damaged.

Different means of adaptation to cold and resistance to freezing are already known in animals and plants.

Thus, certain animals use particularly supercooling to maintain fluids in a liquid condition below 0° C., thanks to the action of proteins with an "anti-freeze" action which prevent the aggregation of ice crystals.

Others carry out a slow solidification of fluids and, in parallel, protection of the cellular membranes by means of proteins that start the formation of extracellular ice and cytoplasmic protective agents.

In vegetation, the resistance to ice consists in fact of an accommodation phenomenon and results from the accumulation in the above ground portions, of protective substances such as sugars, antioxidants and particular proteins, inhibiting the nucleation or permitting controlled inhibition of nucleation of ice crystals.

The problem addressed by the present invention consists, starting from the above observations, in conceiving and obtaining an active composition whose use or application leads to an action of the supercooling type and an action of the accommodation type for ice, by supplying to the target cells (particularly the cutaneous cells), the elements necessary to fight against the effects of cold.

However, it has been determined, in an unexpected and surprising manner, by the inventors, that by associating in a same composition, according to predetermined fractions, two biochemical groups of active substances, namely, on the one hand, certain particular types of monosaccharides and, on the other hand, specific proteins, there can be obtained a complex and stable compound which combines the mentioned actions and simultaneously has preventive, protective and reparative effects as to damages that can result from exposure to cold, particularly to dermal and epidermal cells.

Thus, the present invention has for its object a composition active against the effects of cold, characterized in that it is comprised by a mixture of at least a polysaccharide, amino acids and proteins or simple proteins.

This active composition can preferably be constituted essentially by 0.1 to 30% by weight of at least one polysaccharide, 45% to 95% by weight of proteins or simple proteins and by 0.1% to 25% by weight of amino acids.

According to a first characteristic of the invention, the polysaccharide at least present comprises at least one mucilage extracted from plants and belonging preferably to the family of arabinogalactanes, particularly conifer extracts or of plants such as corn.

This type of substance has properties that are anti-dehydrating, cryoprotective and inhibitive of the growth of ice crystals.

According to a preferred embodiment of the invention, the composition can comprise, as polysaccharides, between 0.1% and 10% by weight of glycogen and between 0.1% and 20% by weight of mucilage, particularly extracts of conifers, more particularly of larch. The glycogen preserves the viability and vitality of the cells, even when frozen, and constitutes a source of energy because of its possible conversion into glucose, even at low temperature.

According to another characteristic of the invention, the active composition preferably comprises between 45% and 95% by weight of vegetable proteins extracted from legumes, particularly soya, peas, green beans, lupine, beans, chick peas or the like.

These thermostable polypeptide fractions have properties to inhibit the crystallization of water ("anti-freeze" activity), as well as anti-radical and anti-oxidant properties.

The specific amino acids integrated into the active composition according to the invention should preferably give rise to an osmotic action and should be selected, for example, from the group consisting of threonine, serine, proline and alanine.

According to a preferred embodiment of the invention, the active composition comprises, on the one hand, between 0.1% and 20% by weight of proline and, on the other hand, between 0.1% and 5% by weight of alanine.

It has been determined that the different specific constituents of the active composition as described above, combine their effects and confer on said composition remarkable properties, substantially better than those resulting from the simple addition of their separate effects.

Thus, said active composition, applied to the skin, acts by a triple action, namely, on the one hand, as a cellular protector, by inhibiting the damage arising from cold to the cells, their membranes, their organelles and their functions, on the other hand, as a protector and cutaneous reparative against the damages connected with cold (action against cutaneous drying, lack or loss of flexibility or elasticity, discomfort, tightness or the like) and, finally, as an inducer of a potentialization of the cellular defenses against the effects of cold or freezing.

For the description of several practical exact embodiments of active compositions according to the invention, there are indicated hereafter different examples of composition, given purely by way of illustration and not to be limiting.

EXAMPLE 1

| | |
|---|---|
| Soya proteins | 77% |
| L-Proline | 13% |
| L-Alanine | 3% |
| Glycogen | 4% |
| Larch extract rich in mucilage | 3% |

EXAMPLE 2

| | |
|---|---|
| Pea proteins | 80% |
| L-Proline | 10% |
| L-Alanine | 4% |
| Glycogen | 2% |
| Larch extract rich in mucilage | 4% |

EXAMPLE 3

| | |
|---|---|
| Lupin proteins | 60% |
| L-Proline | 10% |
| L-Alanine | 5% |
| Glycogen | 5% |
| Larch extract rich in mucilage | 20% |

The present invention also has for its object a protective and reparative cosmetic product, adapted to be applied to the skin, characterized in that it comprises an active composition as described above, particularly with a constituent fraction comprised between 1% and 50% by weight.

Preferably, this cosmetic product will comprise between 5% and 10% by weight of active composition according to the invention.

By way of non-limiting example of practical embodiments of the invention, there will be described hereafter different cosmetic products or preparations for topical use for the skin, comprising a predetermined quantity of the active composition described above and compatible with such an application.

EXAMPLE 1

A cosmetic product in the form of a solar cream adapted for use during winter sports and according to the invention could for example have a weight composition constituted from the following fractions A, B and C as indicated hereafter.

| | |
|---|---|
| Fraction A | |
| Cetyl alcohol | 2.000 |
| Capryl and capric triglyceride | 9.000 |
| Paraffin oil | 3.750 |
| Liquid lanolin | 1.000 |
| Dimethicone | 0.250 |
| Octyldodecanol | 1.500 |
| LS ceramides | 0.500 |
| Benzophenone-3 | 4.500 |
| Octyl methoxycinnamate | 7.500 |
| Preservative | 0.300 |
| Fraction B | |
| Water | 58.200 |
| Preservative | 0.300 |
| Glycerine | 3.000 |
| Potassium cetyl phosphate | 3.000 |
| Fraction C | |
| Active composition according to the invention | 5.000 |
| Perfume | 0.200 |

The process of preparing and producing face cream above consists essentially in heating fraction A and fraction B to 80° C., introducing fraction A into fraction B with high speed agitation (by means of a turbine) while maintaining the mentioned temperature, cooling the mixture to 45° C. while maintaining agitation, adding thereto fraction C and finally bringing the final preparation obtained to ambient temperature, with planetary agitation.

EXAMPLE 2

An emulsion for the face and day care protection, according to the invention, could for example have a weight composition constituted from the following fractions A, B and C as indicated hereafter.

| | |
|---|---|
| Fraction A | |
| Cetyl alcohol | 2.500 |
| Sorbitan palmitate | 3.500 |
| Glycerol stearate | 1.500 |
| Stearylic and cetylic isononanoate | 7.000 |
| Octyldodecanol | 5.500 |
| Paraffin oil | 3.000 |
| Dimethicone | 2.000 |
| Fraction B | |
| Water | 62.100 |
| Preservative | 2.500 |
| Glycerin | 4.000 |
| Sodium stearyl and cetyl sulfate | 1.200 |
| Fraction C | |
| Active composition according to the invention | 5.000 |
| Perfume | 0.200 |

The process for preparation and production of the emulsion for the face described above is substantially identical to the process described with respect to Example 1.

EXAMPLE 3

A cosmetic product in the form of a hand cream, according to the invention, could for example have a weight composition constituted from the following fractions A, B and C as indicated hereafter.

| | |
|---|---|
| Fraction A | |
| Sodium sulfate cetostearylic and cetyl/stearyl alcohol | 7.000 |
| Stearic acid | 1.000 |
| LS ceramides | 0.500 |
| Octyldodecanol | 2.500 |
| Fraction B | |
| Water | 43.500 |
| Preservative | 0.300 |
| Glycerin | 40.000 |
| Fraction C | |
| Composition according to the invention | 5.000 |
| Perfume | 0.200 |

The process of preparation and production of the hand cream described above is substantially identical to the process described with respect to Example 1.

Of course, the invention is not limited to the embodiments described. Modifications remain possible, particularly as to the nature of the various elements or by substitution of technical equivalents, without thereby departing from the scope of protection of the invention.

What is claimed is:

1. Topical active composition against the effects of cold, which comprises 0.1% to 30% by weight of polysaccharides comprising at least glycogen and at least one mucilage extracted from conifer, by 45% to 95% by weight of vegetable proteins extracted from legumes and by 0.1% to 25% by weight of amino acids selected from the group consisting of threonine, serine, proline and alanine.

2. Topical active composition according to claim 1, which comprises, as polysaccharides, between 0.1% and 10% by weight of glycogen and between 0.1% and 20% by weight of arabinogalactanes mucilages extracted from conifer.

3. Topical active composition according to claim 1, wherein the mucilages are present in the form of extracts of larch.

4. Topical active composition according to claim 1, which comprises between 45% and 95% by weight of vegetable proteins extracted from soya, peas, green beans, lupin, beans or chick peas.

5. Topical active composition according to claim 1, which comprises between 0.1% and 20% by weight of proline and between 0.1% and 5% by weight of alanine.

6. Protective and reparative cosmetic preparation, adapted to be applied to the skin, which comprises the composition active against the effects of cold according to claim 1.

7. Cosmetic preparation which comprises between 1% and 50% by weight of the active composition according to claim 1.

8. Cosmetic preparation which comprises between 5% and 10% by weight of the active composition according to claim 1.

* * * * *